(12) United States Patent
Ouchi et al.

(10) Patent No.: US 8,440,971 B2
(45) Date of Patent: May 14, 2013

(54) EXAMINING APPARATUS

(75) Inventors: Toshihiko Ouchi, Machida (JP);
Shintaro Kasai, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 14 days.

(21) Appl. No.: 13/142,554

(22) PCT Filed: Dec. 16, 2009

(86) PCT No.: PCT/JP2009/071366
§ 371 (c)(1),
(2), (4) Date: Jun. 28, 2011

(87) PCT Pub. No.: WO2010/076874
PCT Pub. Date: Jul. 8, 2010

(65) Prior Publication Data
US 2011/0267600 A1 Nov. 3, 2011

(30) Foreign Application Priority Data

Jan. 5, 2009 (JP) .................................. 2009-000465

(51) Int. Cl.
*G01J 5/00* (2006.01)
(52) U.S. Cl.
USPC ....................................................... 250/338.1
(58) Field of Classification Search .... 250/338.1–338.5, 250/340, 341.1–341.8
See application file for complete search history.

(56) References Cited

U.S. PATENT DOCUMENTS

| 5,710,430 A | 1/1998 | Nuss |
| 5,939,721 A | 8/1999 | Jacobsen et al. |
| 2001/0029436 A1 | 10/2001 | Fukasawa |
| 2007/0108382 A1 | 5/2007 | Itsuji |
| 2007/0235650 A1* | 10/2007 | Federici et al. ............ 250/341.8 |

FOREIGN PATENT DOCUMENTS

| DE | 10 2007 011 820 A1 | 9/2008 |
| GB | 2446026 A | 7/2008 |
| JP | 2002-098634 A | 4/2002 |
| JP | 3387721 B2 | 3/2003 |

* cited by examiner

*Primary Examiner* — Kiho Kim
(74) *Attorney, Agent, or Firm* — Canon U.S.A., Inc. IP Division

(57) ABSTRACT

In an examining apparatus or method, values of thickness and characteristic of an object, or distributions thereof can be simultaneously acquired. The examining apparatus includes a portion 9 for irradiating an object 2 with radiation, a portion 10 for detecting the radiation from the object, an acquiring portion 26, a storing portion 21 and a calculating portion 20. The acquiring portion acquires transmission time associated with detection time of radiation, and amplitude of the radiation. The storing portion beforehand stores relationship data between the transmission time and amplitude, and representative values of characteristic of the object. The calculating portion obtains values of thickness and characteristic of the object based on the transmission time, amplitude and relationship data.

9 Claims, 14 Drawing Sheets

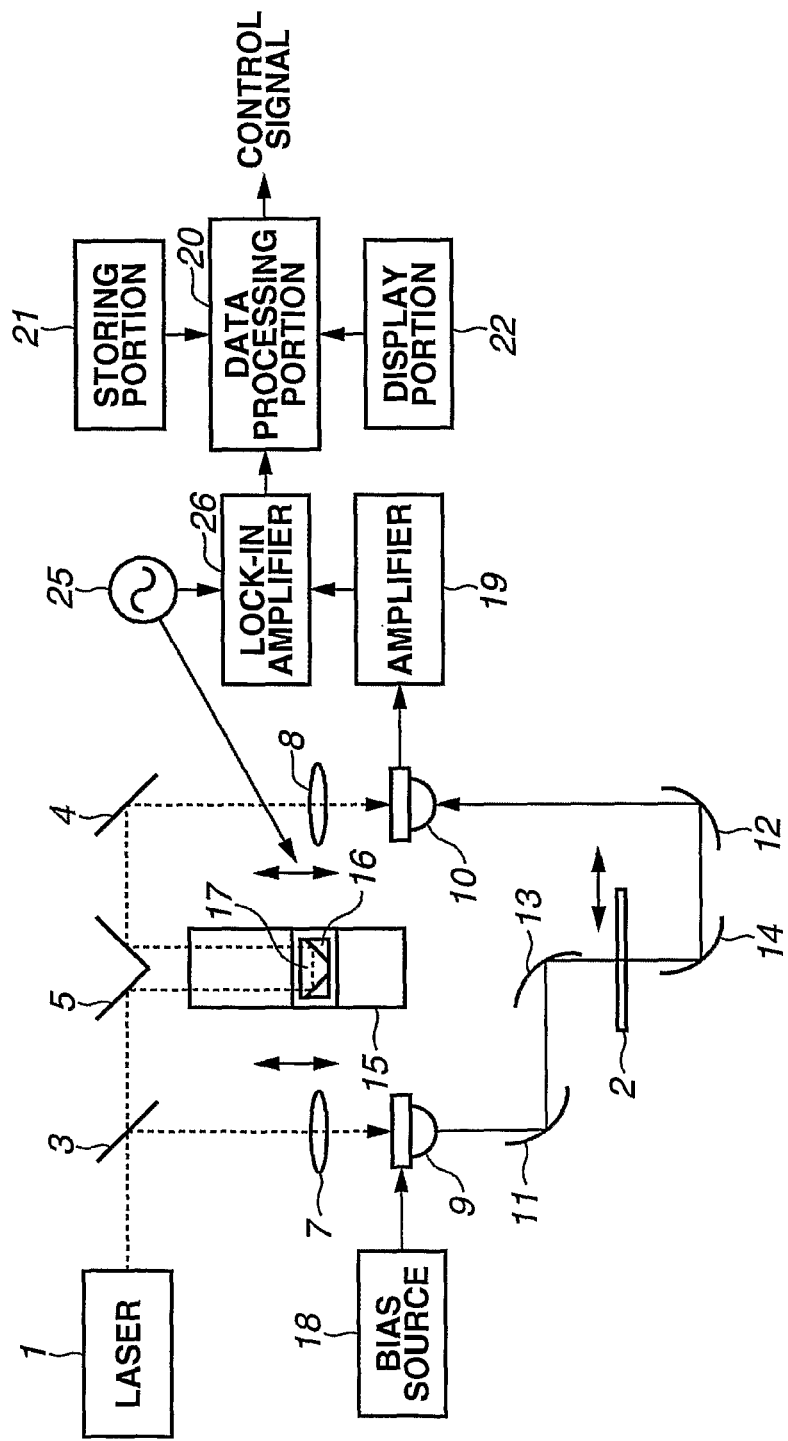

EXAMINING APPARATUS

TECHNICAL FIELD

The present invention relates to an apparatus and method for acquiring information of an object by using electromagnetic wave (hereinafter also referred to as radiation). Particularly, the present invention mainly relates to an examining apparatus for acquiring distributions of characteristic, thickness and the like of an object by using high frequency radiation in a frequency range from millimeter wave to terahertz wave (i.e., in a frequency range between 30 GHz and 30 THz), and a method for driving the examining apparatus.

BACKGROUND ART

In recent years, non-destructive sensing technology using terahertz radiation (hereinafter also referred to as THz wave) has been researched and developed. In this specification, THz wave means radiation containing a component in a frequency band between 30 GHz and 30 THz. Application of an examining apparatus using THz wave to internal examining means for performing non-destructive quality check of an object has been proposed. In other words, applications to inspection of foreign substance in powdery matter, defect examination of plastics molds, examination of carrier concentration of semiconductor wafers, and the like have been proposed.

Japanese Patent No. 3387721 (PTL 1) discloses technology of examination of characteristic of an object that can be executed by spectral analysis achieved by the Fourier transform of a time-domain waveform of THz wave pulse transmitted through the object. The time-domain waveform can be obtained by the THz time-domain spectroscopy (THz-TDS). In this technology, composition characteristic at each point of the object is recognized by comparison between signals acquired and information of data base of substances acquired beforehand, and the point of the object is moved to obtain an image of the composition characteristic of the object.

Further, Japanese Patent Laid-open No. 2002-98634 (PTL 2) discloses technology that composition characteristic of a semiconductor wafer, such as mobility, electric conductivity and carrier concentration, can be calculated from its complex refractive index acquired by the THz-TDS using Drude model. This technology has been developed as non-destructive means for examining a wafer of Si, GaAs or the like.

CITATION LIST

Patent Literature
PTL 1
Japanese Patent No. 3387721
PTL 2
Japanese Patent Laid-open No. 2002-98634

SUMMARY OF INVENTION

Technical Problem

However, the technology of PTL 1 is directed to such that analyzes an object image based on a specific change in the waveform of THz wave pulse transmitted through the object, but not to such that acquires a quantitative value of characteristic of an object, such as its electric conductivity. Actually, in a case where THz wave pulse is transmitted through an object, a change amount of the waveform of THz wave pulse varies depending on its thickness as well as its composition. Accordingly, distribution of relative values of characteristic of the object can be only obtained by the spectral analysis. Further, although the technology of PTL 2 is directed to acquisition of absolute values of mobility, electric conductivity and carrier concentration of a semiconductor wafer, it can be only used in a case of such a wafer as has a precisely uniform thickness that is known beforehand.

Therefore, in a case of a plate-like object whose thickness has not yet been measured, or fluctuates though roughly known, the absolute value of its complex refractive index is difficult to acquire. Thus, it can hardly be said that a distribution of the absolute value of characteristic, such as electric conductivity, can be readily measured.

Solution to Problem

According to one aspect of the present invention, there is provided an apparatus for examining an object, which includes an irradiating portion for irradiating an object with radiation, a detecting portion for detecting radiation from the irradiated object, an acquiring portion, a storing portion, and a calculating portion. The acquiring portion acquires transmission time associated with detection time of the radiation detected by the detecting portion, and amplitude of the radiation detected by the detecting portion. The storing portion beforehand stores relationship data between the transmission time and amplitude, and representative values of characteristic of the object. The calculating portion obtains values of thickness and characteristic of the object based on the transmission time, the amplitude, and the relationship data stored in the storing portion.

The representative value is a value of characteristic or thickness of the object in a predicted variation range from its given standard value. Each value is predicted to vary in the predicted variation range from its given standard value in a fabrication process of the object and the like. In almost all cases where a difference in a state of an object from its known standard state is to be detected to perform feedback control or the like in an examining or fabricating apparatus of the object, the state of the object to be examined or fabricated can be considered to be in a predetermined predicted variation range from its standard state. Therefore, the present invention uses such representative values. Further, the transmission time associated with the detection time of radiation is a time between any standard time and the detection time of radiation detected by the detecting portion. It is, for example, transmission time of radiation from its emission time at the irradiating portion to its detection time at the detecting portion.

According to another aspect of the present invention, there is provided a method for examining an object, which includes a detecting step of detecting radiation from an object irradiated with the radiation, an acquiring step, a storing step, and a calculating step. In the acquiring step, transmission time associated with detection time of the radiation detected in the detecting step, and amplitude of the radiation detected in the detecting step. In the storing step, relationship data between the transmission time and amplitude, and representative values of characteristic of the object is beforehand stored. In the calculating step, values of thickness and characteristic of the object are obtained based on the transmission time and amplitude acquired in the acquiring step, and the relationship data stored in the storing step. The representative value is a value of characteristic or thickness of the object in a predicted variation range from its given standard value.

ADVANTAGEOUS EFFECTS OF INVENTION

According to the present invention, the relationship data between the transmission time and amplitude, and the representative values of thickness and characteristic of an object is beforehand stored. And, based on the transmission time and radiation amplitude acquired from an unknown object, and the stored data, values of thickness and characteristic of the object are obtained. Therefore, for example, imaging of the object can be executed while simultaneously acquiring values of thickness and characteristic of the object, or their distributions.

Further, for example, imaging of two-dimensional distributions of thickness and characteristic of an object can be performed using THz wave, and it is accordingly possible to achieve quality check, screening in a fabrication process, feedback control in a fabrication process, and the like. Thus, improvement of productivity can be attained. Further, non-contact measurement of the absolute value of characteristic, such as resistivity and electric conductivity, of an object can be achieved, and hence the object can be rapidly analyzed without being damaged.

Further features of the present invention will become apparent from the following description of embodiments and exemplary embodiments with reference to the attached drawings.

BRIEF DESCRIPTION OF DRAWINGS

FIG. 1 is a view illustrating an embodiment of an examining apparatus of the present invention.

DESCRIPTION OF EMBODIMENTS

Figure 2A:
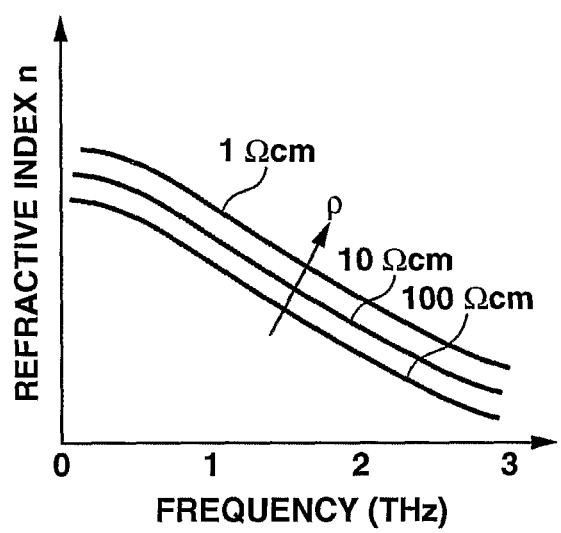
FIG. 2 is a view illustrating operation and the like of an embodiment of an examining apparatus of the present invention.

Description will hereinafter be made of embodiments according to the present invention. An important point of an apparatus and method of the present invention is as follows. Relationship data between transmission time and amplitude to be detected, and representative values of thickness and characteristic of an object is beforehand stored. Based on the transmission time and radiation amplitude acquired from an unknown object, and the stored relationship data, values of thickness and characteristic of the object are obtained.

Based on this concept, fundamental embodiments of an apparatus and method of the present invention have the above-described constructions, respectively. On the basis of the fundamental embodiments, the following embodiments and exemplary embodiments can be constructed. Typically, radiation contains a frequency component in a frequency range between 30 GHz and 30 THz. Further, where radiation is in the form of a pulse, the acquiring portion acquires the transmission time and radiation amplitude using the time domain spectroscopy, the calculating portion compares the transmission time and radiation amplitude detected with the relationship data stored. The characteristic of the object to be acquired by the calculating portion is, for example, electric conductivity, resistivity or the like.

The following constructions are also possible. While a peak time position and a change amount of a peak amplitude acquired by the acquiring portion, that respectively correspond to the transmission time and the radiation amplitude, are stored as a relative position of the object relative to the radiation pulse is moved, values of thickness and characteristic of the object are acquired at each relative position by the calculating portion. And, imaging of distributions of thickness and characteristic of the object is performed. In this imaging, the distributions of thickness and characteristic of the object can be separated from each other by using a spatial filter after the imaging is performed.

Where the object has an absorption property at a specific frequency, the construction can be made as follows. The storing portion beforehand stores amplitude at the specific frequency as the radiation amplitude, and the calculating portion acquires values of thickness and characteristic of the object based on the amplitude at the specific frequency acquired by the acquiring portion and the relationship data stored.

Further, a method of driving an apparatus for performing imaging of distributions of values of thickness and characteristic of an object using the radiation pulse can include a moving step, a controlling step, and a storing step. In the moving step, the relative position between the object and the radiation pulse is moved. In the controlling step, a delay position of a delay portion used in the time domain spectroscopy is feedback-controlled so that a peak time position of the radiation pulse can be always maintained to be acquired in the move step and the peak time position can be acquired. In the storing step, the delay position feedback-controlled in the controlling step is stored.

Embodiments will be described with reference to the drawings. FIG. 1 illustrates an embodiment of an examining apparatus of the present invention. Its fundamental construction is the same as a general THz-TDS apparatus described in Patent Citation 1.

In the construction of FIG. 1, a femtosecond laser 1 capable of generating radiation pulse of about 80 femtoseconds at a wavelength of 800 nm emits laser light, and the laser light is divided into two by a beam splitter 3. One light is condensed by a lens 7, and guided to a photoconductive device 9 to generate THz wave pulse with a pulse width of about 500 femtoseconds. In the photoconductive device 9, an antenna is formed on a LT-GaAs (low-temperature-grown galliumarsenide). THz wave can also be generated directly from a crystal surface of semi-insulating GaAs, InP, ZnTe, GaSb or the like. A bias voltage is applied to the photoconductive device 9 on the generation side by a power source 18. Typically, a DC voltage of about 10 V is applied. As the voltage value increases, the intensity of THz wave increases. Depending on the configuration, saturation property appears at a certain voltage.

The other laser light is guided onto a photoconductive device 10 through a reflective mirror 5, a delay portion including drive stages 15 and 16 and a retro-reflector 17 placed on the stage 16, a mirror 4, and a lens 8. This laser light is used as a gate signal for detecting the THz wave. THz wave generated by the photoconductive device 9 is applied to an object 2 through parabolic mirrors 11 and 13. THz wave transmitted through the object 2 is condensed on the photoconductive device 10 on the detection side through parabolic mirrors 14 and 12. Detection of the THz wave can also be performed by using an electro-optic (EO) crystal or the like.

THz wave pulse generated by the photoconductive device 9 is shaped into a spot with a diameter of about 1 mm by the parabolic mirrors 11 and 13, and the spot is illuminated on the object 2. THz wave transmitted through the object 2 is coupled to the photoconductive device 10 on the detection side by the parabolic mirrors 14 and 12. To acquire transmission image of the entire object, the object 2 is moved in a two-dimensional manner, i.e., in a direction indicated by an arrow in FIG. 1 and a direction perpendicular to a sheet of FIG. 1, for example. Alternatively, to obtain the two-dimensional image, the THz wave beam can be scanned by a galvano-mirror or the like without moving the object 2.

Description will be made of an embodiment of a method of simultaneously acquiring thickness and electric conductivity of an object. In this embodiment, it is assumed that a difference from a standard state of a known object is detected, and the detected result is used for feedback control or the like of a product examining or fabricating apparatus in a plant or the like.

Figure 2B:
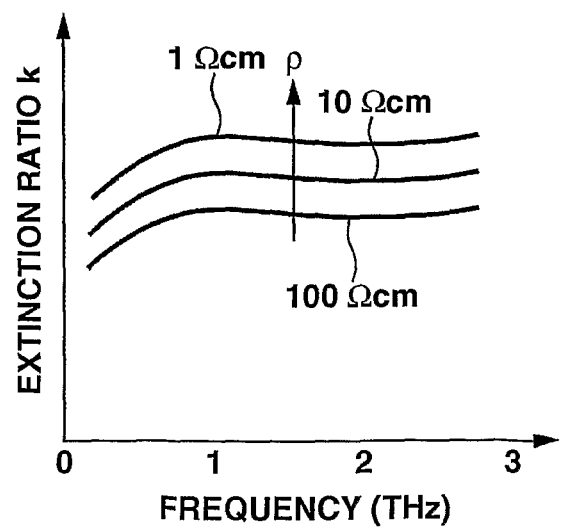

For example, examination of a conductive sheet with a thickness of 100 microns and volume resistivity of 10 Ωcm is performed. Initially, sheets with resistivity, for example, between 100 Ωcm and 1 Ωcm are produced, and their resistivity dependencies of complex refractive index are beforehand measured using a THz-TDS apparatus. The resistivity is separately calibrated by using a resistivity measuring device. FIG. 2A and FIG. 2B show the measured results. In these graphs, three results (in other words, relationship data with three representative values of resistivity ρ being used as parameter) are shown, respectively. Actually, data for interpolation between these three values is also acquired.

On the other hand, where an object is to be actually examined, the following correlation formulae hold between amplitude ratio, phase difference, real part n and imaginary part k of the complex refractive index, and thickness d of the object. The amplitude ratio and phase difference can be obtained by performing FFT (fast Fourier transformation) of THz wave pulse transmitted through the object, and the result obtained without the object being placed is used as reference. Suffixes of sam and ref represent object and reference, respectively.

$$|E_{sam}(\omega)|/|E_{ref}(\omega)|=\{4n^*\exp(-k\omega d/c)\}/(1+n)^2 \quad (1)$$

$$\theta_{sam}-\theta_{ref}=(n-1)\omega d/c \quad (2)$$

E is the electric field amplitude, θ is the phase, ω is the angular frequency of THz wave, and c is the light velocity.

The complex refractive index for each representative resistivity of the object to be examined is beforehand acquired and known. This data is stored in a storing portion 21 in FIG. 1. An object with resistivity in a range of the data stored can be examined as follows. In a data processing portion 20, a value of the thickness d in formulae (1) and (2) is successively changed from a value that is considered to be near the actual thickness, and the value of the thickness d is converged so that the complex refractive index calculated from formulae (1) and (2) is fitted to the data (such as illustrated FIG. 2A and FIG. 2B) stored in the storing portion 21. Thereby, thickness d and resistivity ρ can be obtained from the fitting result. Such acquisition can be used because a predetermined relationship (i.e., Kramers-Kronig relations) holds between real part and imaginary part of the complex refractive index even if the value of a certain kind of characteristic, such as resistivity, of the object fluctuates. Accordingly, values of n and k are not independent from each other, and the number of unknown values is actually single. Therefore, if two parameters (two unknown values) of amplitude ratio and phase difference can be measured using the THz-TDS, thickness d and n (and k), or a value of characteristic, such as resistivity ρ, capable of being derived from n and k can be obtained by the processing portion 20. The result can be displayed on a display portion 22.

Where an object to be examined has an approximately uniform composition and its resistivity or the like does not fluctuate so largely, the calculation can be executed quite readily. Because of the principle of the present invention as described above, an object capable of analysis is limited to a certain kind. An object to be examined must satisfy conditions as follows. Representative values of the object, such as values of complex refractive index or characteristic capable of being derived therefrom, in a certain range, can be beforehand measured and stored, and the stored value can be picked out to be compared with measured values of each object.

More favorably, fluctuations of thickness and value of characteristic to be examined are not so large. In such a case, when a THz wave pulse waveform hardly changes in a time domain, calculation process and examination time can be reduced. This is because the pulse waveform only changes with a similar shape being maintained, and measurement of time shift Δt and change ΔA in peak amplitude is only needed. In other words, in such a case, when a corresponding look-up table between (Δt, ΔA) and (Δd, Δρ) is beforehand made as a shift from standard values, a shift from the standard value is to be calculated only at an initial measurement point, using the above-described fitting method. Two-dimensional scan data thereafter can be obtained by measuring only the peak time shift and the change in peak amplitude from initial values. Accordingly, distributions of values of thickness d and resistivity ρ can be rapidly acquired as, for example, the two-dimensional image, and the object can be rapidly examined.

With respect to the value of characteristic to be acquired, electric conductivity, carrier concentration, mobility and concentration of composition matter capable of being correlated with n and k can also be obtained, for example.

Description will be made with reference to FIG. 1, of an embodiment of the examining apparatus wherein only data series of Δt and ΔA is acquired for imaging to rapidly acquire a two-dimensional distribution image. The delay system is comprised of two stages. A stage 15 is a first stage capable of scanning over a long stroke of above 10 mm at a relatively low speed. A stage 16 is a second stage capable of rapidly vibrating with amplitude of below 100 microns at a frequency between about several kHz and about 100 kHz. The frequency depends on the amplitude. As driving means for the first stage 15, various kinds of motors, supersonic methods, electromagnetic methods or the like can be favorably used. On the other hand, piezoelectric actuator, MEMS device or the like can be used as driving means for the second stage 16. In the second stage 16, the vibration speed can be increased by using a rotary driving system in place of the linear driving system. For example, rotation of a prism in a prism transmission system is controlled to change an incident angle of THz wave on the prism. The transmission distance of THz wave through the prism is thereby changed, and the time delay can be rapidly changed.

Figure 3A:
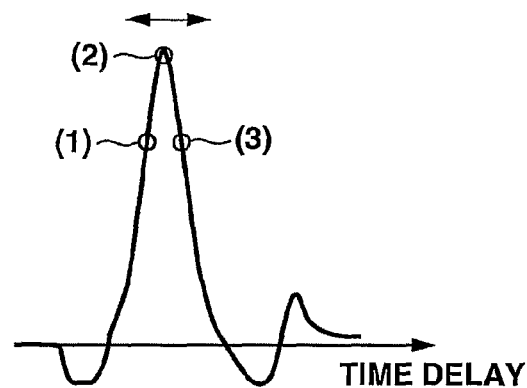
FIG. 3 is a view illustrating a signal acquiring method using a minute vibration.

The operation of the first stage 15 is similar to that of a general THz-TDS. For example, a pulse corresponding to a time delay of 40 picoseconds can be observed with a scan stroke of 6 mm. For detection of a time-domain waveform, a voltage of the electric power source 18 is modulated at about 1 kHz, and an output from the photoconductive device 10 is detected by using amplifier 19 and lock-in amplifier 26. This step is necessary where the time-domain waveform is to be acquired, or a peak position is to be sought at an initial measurement setting. A portion of the time-domain waveform obtained at the time is a pulse as illustrated in FIG. 3A.

Where only a peak is to be detected, lock control of the peak position is performed by using the short-stroke second stage 16. In other words, a rapid vibration at frequency above several kHz with amplitude below a distance corresponding to the pulse width is executed in the second stage 16. By using an oscillator 25 acting as a signal source of the above vibration and the lock-in amplifier 26, synchronous detection is performed. Thereby, on the detection side, only the modulating signal component can be electrically picked out, and the peak position can be measured with reduced noise and high sensitivity. The measuring principle will be described with reference to FIG. 3.

Figure 3B:
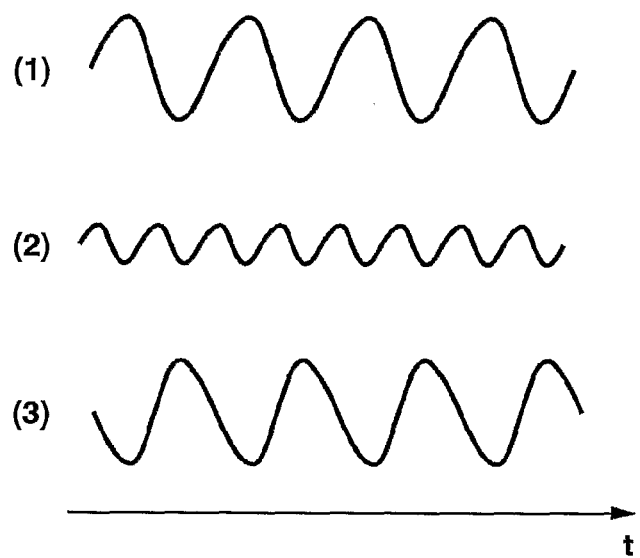
Figure 3C:
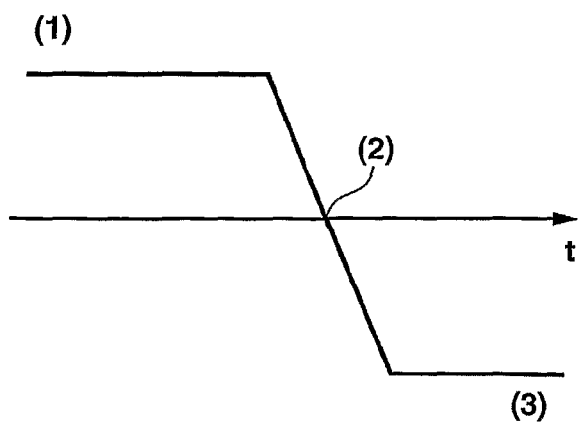

The vibration with a minute amplitude in the second stage 16 corresponds to reciprocating motion of the time delay of the pulse signal in FIG. 3A with amplitude below the pulse width. In this case, a signal to be detected varies depending on the location of a center position of the vibration; (1) location on a positive slope of the pulse, (2) a peak position of the pulse, or (3) location on a negative slope of the pulse. FIG. 3B illustrates signals to be detected. For example, when the modulation is performed with a sinusoidal wave at 10 kHz, intensity modulating signals at 10 kHz with phases having a 180-degree difference therebetween are obtained at locations (1) and (3), respectively. At the time, the first stage 15 is paused. When the vibration is performed about the peak position, a signal at a double frequency of 20 kHz appears. Accordingly, by using a low pass filter of 10 kHz (in this case a system differs from that of FIG. 1), or by picking out a component of 10 kHz using synchronous detection by the lock-in amplifier 26, the magnitude of amplitude changes as illustrated in FIG. 3C. In other words, the peak position can be detected as a zero crossing point at which plus and minus are interchanged.

Figure 2C:
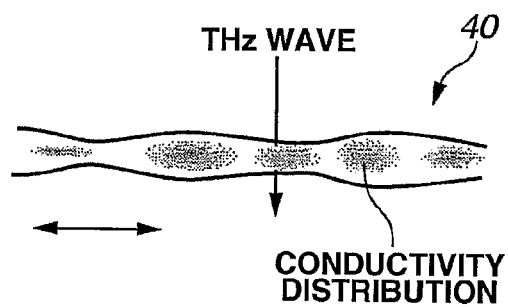
Figure 2D:
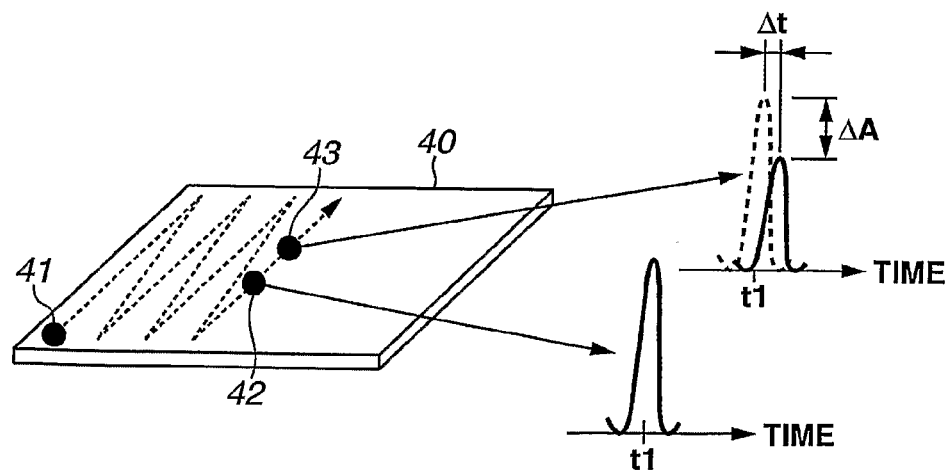

When the measurement point of the object is moved to measure another point, the first stage 15 is feedback-controlled so that the above synchronous detection signal maintained at zero (0). At this moment, the shift time of the THz wave pulse due to the move of the measurement point can be obtained from the amount of shift of the first stage 15 at a stable point. Simultaneously, the magnitude of the signal detected at this moment is the peak amplitude of the THz wave pulse.

Where the two-dimensional measurement is to be executed, the above operation is repeated over an examination region of the object. As illustrated in FIG. 2C, when a sheet-like object 40 with a distribution of electric conductivity is to be examined, lock control of the peak position of THz wave pulse is executed while scanning is performed from an initial measurement point 41. During the scan, time shift amount $\Delta t$ and amplitude change amount $\Delta A$, for example, between measurement points 42 and 43 illustrated in FIG. 2D are measured. Based on these measured amounts, the data processing portion 20 (see FIG. 1) can rapidly acquire distributions of sheet thickness d and resistivity $\rho$, and can supply them to the display portion 23. The display portion is not always necessary. When production management is to be executed in a plant or the like, screening of products can be performed based on a control signal supplied from the data processing portion 20, for example. Further, based on such control signal, physical conditions, such as extrusion molding pressure, temperature and speed, can be feedback-controlled to fabricate structure with high uniformity, for example.

Conventionally, for example, when two-dimensional resistivity distribution of such a sheet-like object is to be measured, a contact-type resistivity measuring device needs to be scanned on the object. Accordingly, there are issues that a considerable measuring time is necessary, and the structure of the object can be damaged. In the above apparatus and method of the present invention, quality management of such conductive sheet material or the like can be rapidly achieved in a simple manner, leading to quality improvement of products.

Figure 6A:
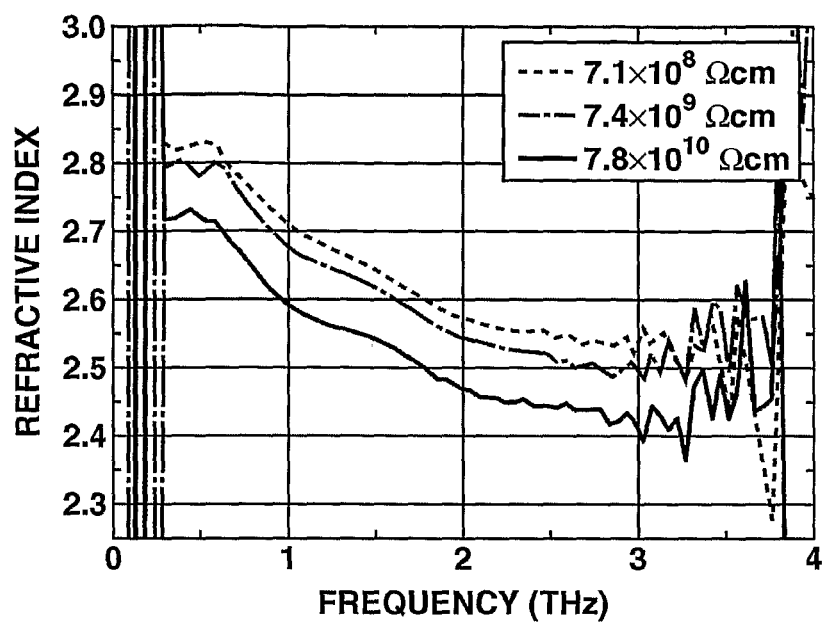
FIG. 6 is a view illustrating graphs for explaining embodiments of an examining apparatus of the present invention.
Figure 6B:
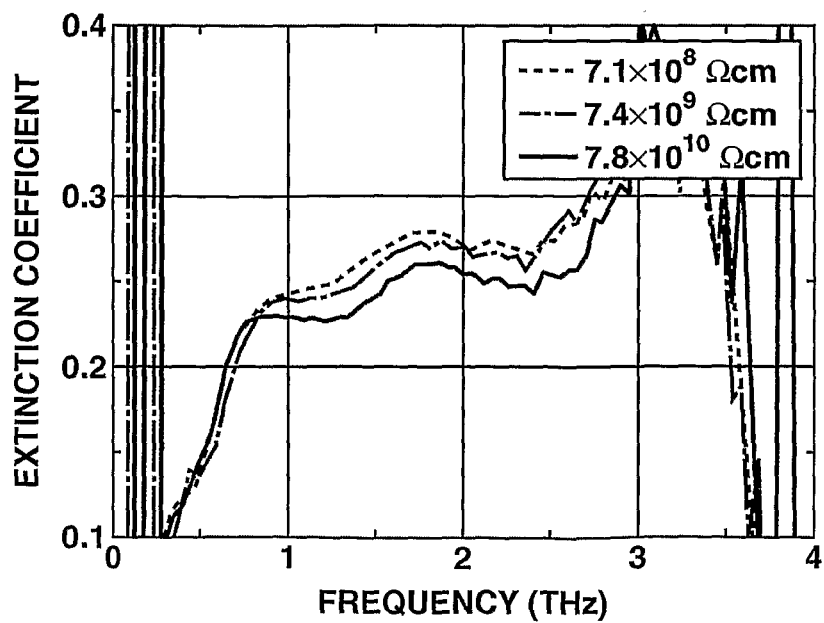
Figure 6C:
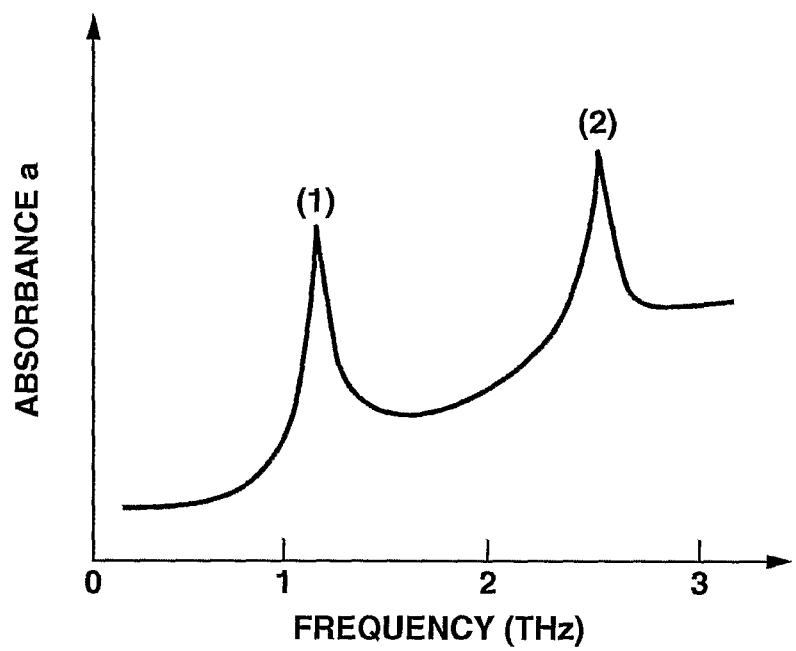

Another embodiment the present invention will be described. In this embodiment, an object is examined using information in a characteristic frequency range. Some objects have frequency bands with characteristic absorption. FIG. 6C schematically illustrates an example of absorbance spectrum. There are characteristic absorption peaks at about 1.1 THz and about 2.6 THz. Under a certain condition (composition concentration is not excessively large, and there is no concentration distribution in a thickness direction), absorbance a at each peak changes approximately in accordance with the Lambert-Beer law.

$$a = \alpha n d \qquad (3)$$

where $\alpha$ is the molar absorption coefficient, n is the concentration, and d is the transmission length.

Figure 6D:
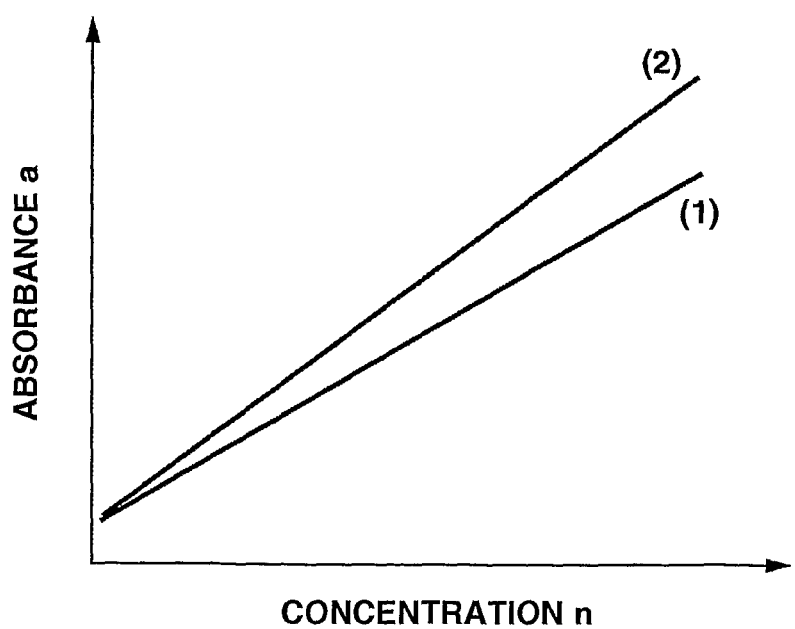

In such a case, the object can be examined based on data base acquired beforehand as in the above-described method. For example, the amount of absorption at 1.1 THz changes depending on the concentration n of composition contained in the object, provided that the thickness d is determined. Therefore, with respect to objects with thicknesses of representative values, it is possible to acquire time-domain waveforms thereof for various concentrations, and obtain absorbance spectra therefrom by the Fourier transform. Thereby, a change of absorbance at the characteristic frequency dependant on the concentration can be obtained. Such change is illustrated in FIG. 6D. As the concentration increases, the absorbance proportionately increases.

Figure 4A:
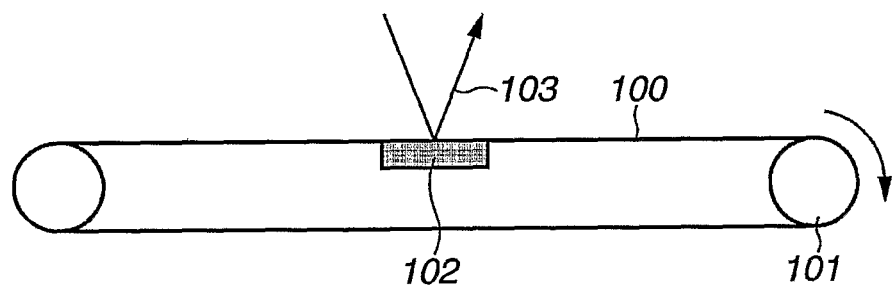
FIG. 4 is a view illustrating embodiments of an examining apparatus of the present invention.
Figure 4B:
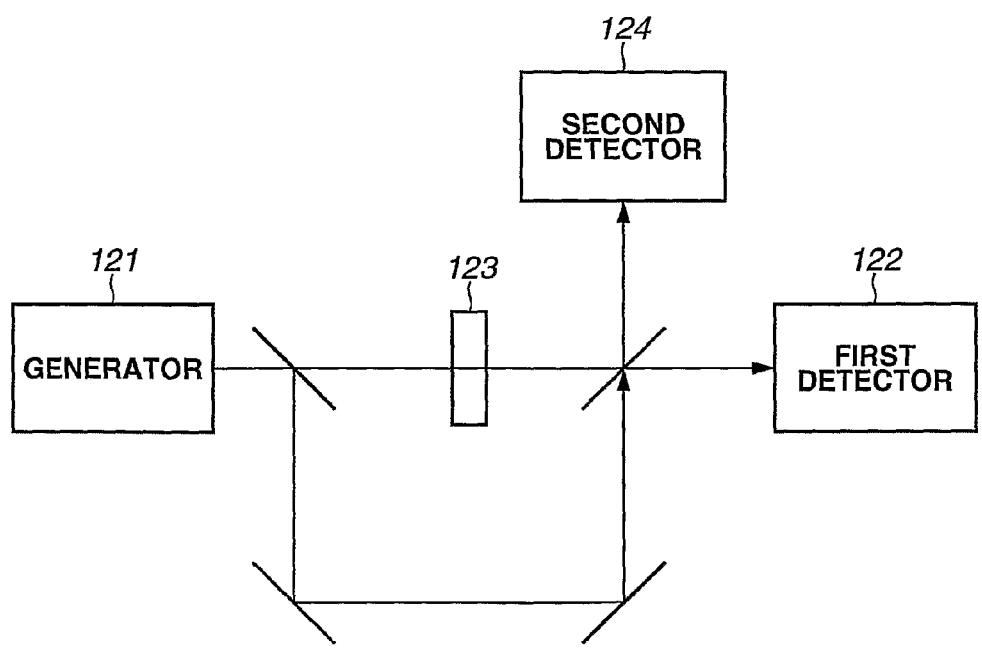

In such a case, while the measurement position is moved as illustrated FIG. 2C and FIG. 2D, only data at an aimed frequency, for example, 1.1 THz is stored. Thus, data to be accumulated can be reduced. There are some methods of measuring the absorbance at a specific frequency. In the THz-TDS method, a time-domain waveform is acquired, and FFT is executed to obtain data series of absorbance at the specific frequency and time difference or phase difference. Alternatively, as illustrated in FIG. 4B, an object 123 is irradiated with THz wave at 1.1 THz from a generator 121, such as quantum cascade laser or resonant tunnel diode laser. And, transmission intensity and time difference due to transmission through the object are detected by detectors 122 and 124 such as micro bolometer or Schottky barrier diode. In this case, to acquire the phase difference, THz wave transmitted through the object is combined with THz wave without being transmitted through the object, as illustrated in FIG. 4B, and interference measurement is performed using an intensity change due to balance detection of two detectors. Here, a path of one THz wave is changed by a delay optical system (not shown). The absorbance and time difference or phase difference can be obtained by appropriately processing signals from two detectors in the processing portion. Here, where a detector with some characteristic is used (for example, in a case of a detector, such as bolometer, incapable of detecting phase information), it may be necessary to obtain and process measured values while moving the detector.

Since the phase difference varies depending on the composition concentration and the thickness of the object, the relationship between the absorbance and phase difference, and shifts of thickness and composition concentration of the object from standard values is to be beforehand acquired and stored. Thereby, distributions of thickness Δd and concentration Δn can be obtained from measured values of absorbance difference Δa and phase difference Δθ (or time difference Δt). The thickness d of the object at the initial position can be accurately measured by a separate method. Alternatively, where a graph as illustrated in FIG. 6D is beforehand acquired with respect to objects having thicknesses of plural representative values, thickness d and concentration n at the initial position can be obtained from measured values of absorbance at plural characteristic frequencies at the initial position, using the above-described fitting method.

This embodiment can be applied to an object with a broad absorption band in a frequency range, as well as the above object with a specific absorption peak whose linewidth is relatively narrow.

More specific embodiments will be described referring to the drawings. A first exemplary embodiment relates to a THz wave transmission examining apparatus wherein a delay system is comprised of two stages as illustrated in FIG. 1. Here, a femtosecond laser of 80-femtosecond pulse width using solid such as titanium sapphire crystal is used, but not limited thereto. According to a spectral band of THz wave to be acquired, a very narrow pulse width, for example, about 10 femtoseconds, can also be used.

In the first exemplary embodiment, a stepping motor is used in the first stage 15, and a piezoelectric actuator is used in the second stage 16. As described above, the second stage 16 executes rapid modulation for wobbling control. For example, rapid modulation at 10 kHz with amplitude (peak to peak) of 3 microns causes modulation of time delay of 20 femtoseconds. The first stage 15 is feedback-controlled to capture the THz wave pulse while locking in the THz wave pulse peak is maintained.

Figure 5:
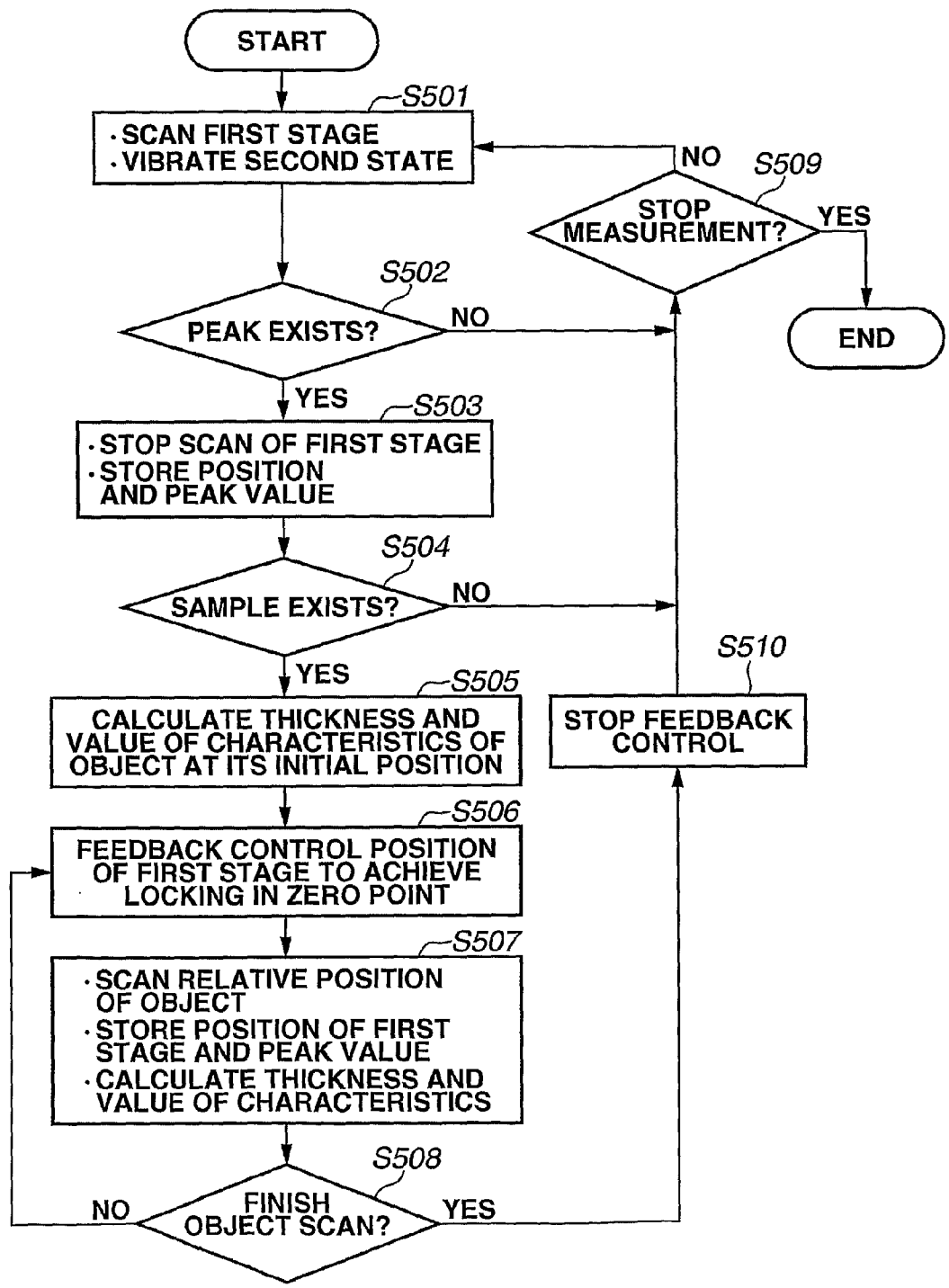
FIG. 5 is a flow chart illustrating an embodiment of an examination process.

Measuring steps are shown in the flow chart of FIG. 5. Prior to measurement of an object, scan of the first stage 15 is performed while the second stage 16 is minutely vibrated to detect the pulse peak under condition without a sample object (S501). The first stage 15 continues to be scanned until the zero crossing point is found and the peak is recognized (S502). If the peak is found to exist, scan of the first stage 15 is stopped, and reference time position of the pulse and value of the pulse peak are stored (S503).

Then, the object is inserted, and the same operation as described above is executed after the measurement point reaches an initial position (see position 41 in FIG. 2D) (S504). That is, the first stage 15 is scanned while the second stage 16 is minutely vibrated. When the zero crossing point is found and the peak is recognized, scan of the first stage 15 is stopped. At the time, time position of the initial position is stored. In next step (S505), the first stage 15 is scanned to obtain a time-domain waveform at the initial position, and thickness and value of characteristic are calculated using the above-described fitting method.

Then, the position of first stage 15 is feedback-controlled while the second stage 16 is minutely vibrated so that capture of the zero crossing point is always maintained (S506). At the same time, position of the object is moved. At this moment, shift Δt of time position of the first stage 15 from its initial time position and shift ΔA of peak amplitude of the THz wave pulse from its initial amplitude are stored (S507).

Figure 7A:
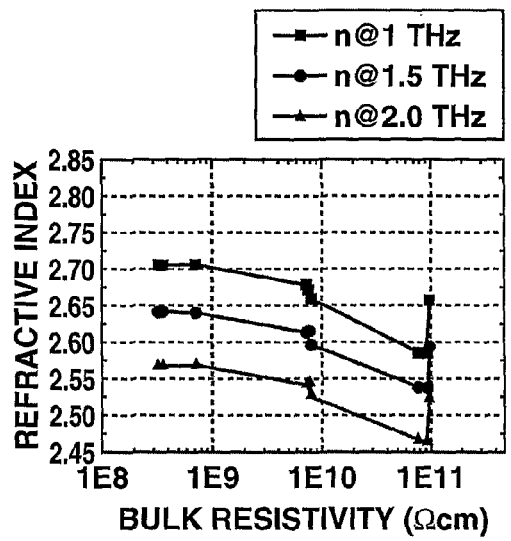
FIG. 7 is a view illustrating graphs for explaining relationships between resistivity and complex refractive index of an embodiment of the present invention.
Figure 7C:
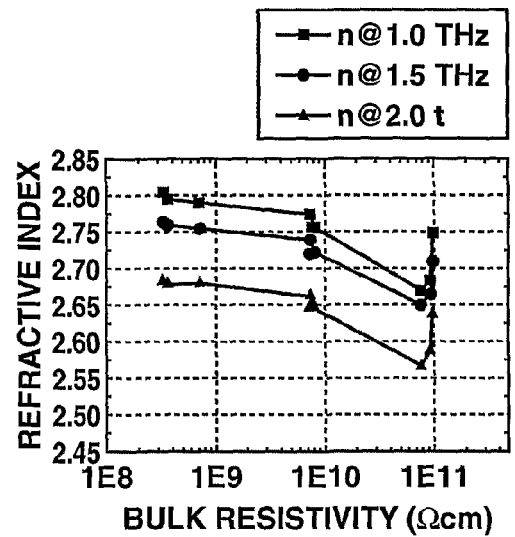
Figure 7B:
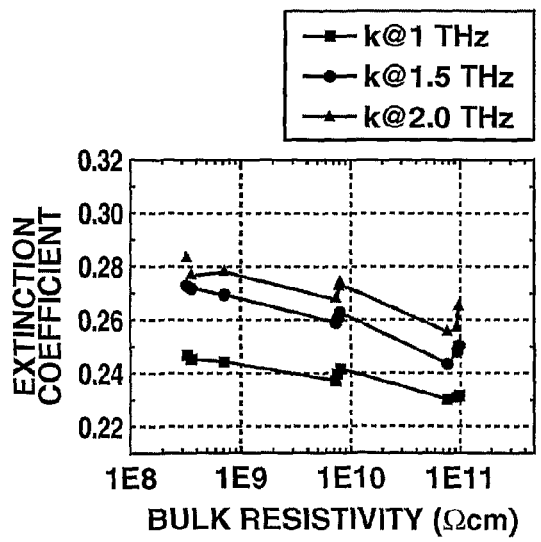
Figure 7D:
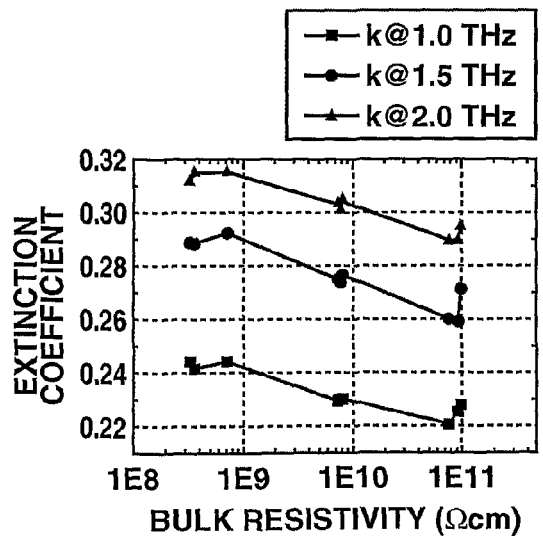

In the first exemplary embodiment, examination is performed to conductive synthetic resin material with thickness of about 80 microns and relatively high resistivity of about $10^{10}$ Ωcm. FIG. 6A and FIG. 6B show an example of characteristic of this material acquired beforehand. Relationships between resistivity and refractive index (real part of complex refractive index), and between resistivity and extinction coefficient (imaginary part of complex refractive index refractive index) are shown. Such data can be obtained by using THz transmission measurement of material with known thickness in the apparatus illustrated in FIG. 1. By using the resistivity as parameter, complex refractive index is derived from the above formulae (1) and (2). FIG. 7 shows graphs made from graphs of FIG. 6A and FIG. 6B. By selecting frequencies of 1 THz, 1.5 THz and 2 THz as parameter, correlations between resistivity, n and k are illustrated. Based on these correlations, look-up tables are made and stored so that (Δd, Δρ) can be obtained from (Δt, ΔA). FIG. 7A and FIG. 7B show values of n and k for THz wave in a certain polarization direction. FIG. 7C and FIG. 7D show values of n and k for THz wave in a polarization direction orthogonal to the above polarization direction. Characteristics are slightly different between these mutually-orthogonal polarization directions. Anisotropy of the object can also be examined by analyzing measured signals based on data including these characteristics relevant to polarization directions.

Thickness d and resistivity ρ at the initial position of the object can be acquired as follows. Measurement results without object are used as reference, and standard values of d=80 microns and ρ=$10^{10}$ Ωcm are used as initial values. And, thickness d and resistivity r can be acquired by the above-described fitting method wherein fitting is performed toward the beforehand-acquired complex refractive index spectrum for each resistivity as illustrated in FIG. 6A or FIG. 6B. Shift values at the initial position from the standard values can be acquired by the above operation. Accordingly, based on shifts Δt and ΔA from the initial values measured while the object is moved as illustrated in FIG. 2C and FIG. 2D, surface distributions of shifts Δd and Δρ from standard values can be calculated. Imaging is also possible based thereon.

Figure 8A:
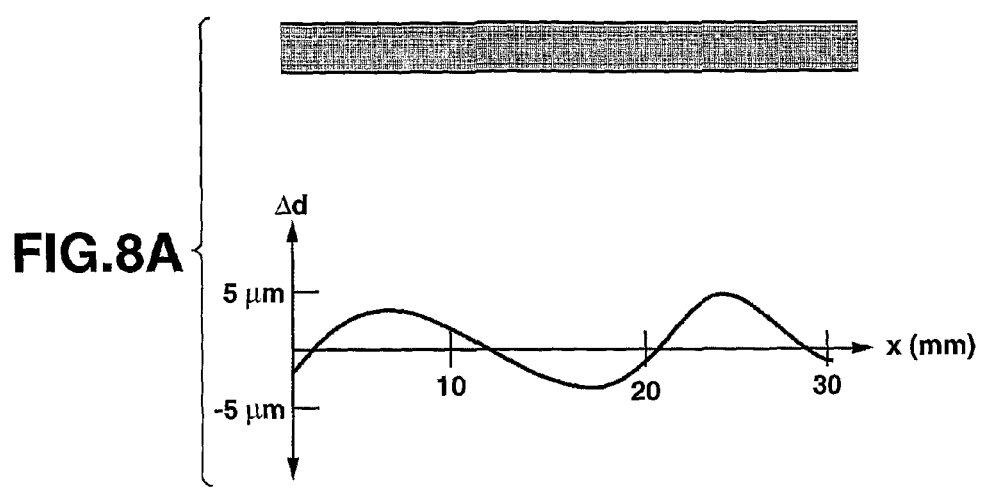
FIG. 8 is a view illustrating graphs and the like for explaining an embodiment of the present invention.
Figure 8B:
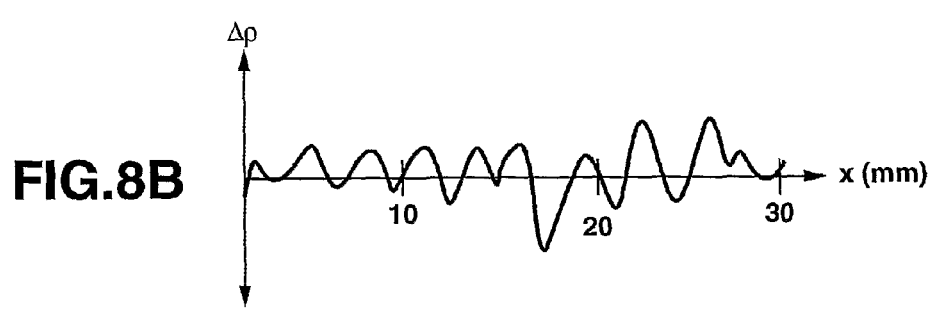
Figure 8C:
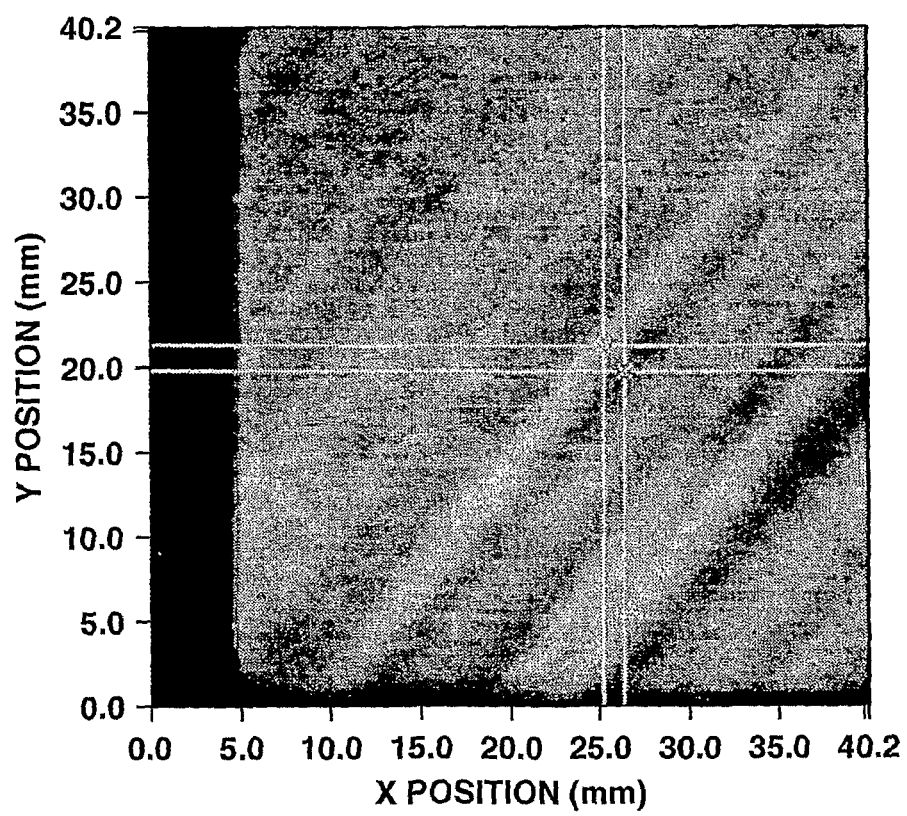

FIG. 8C illustrates an example of such image. Black and white stripes in sub-millimeter order can be observed. This image shows the resistivity distribution, and resistivity thereof fluctuates in a range between $10^9$ Ωcm and $10^{11}$ Ωcm. White portion exhibits a portion with high transmittance and high resistivity. FIG. 8B is a cross-sectional view of the resistivity distribution. In contrast thereto, thickness distribution of the object varies with a moderate period of 10-mm order and variation width of about 5 microns, as illustrated in FIG. 8A.

Such an examining apparatus for executing imaging of an object can be used in a fabrication line of products. Further, based on the control signal from such an examining apparatus, physical conditions, such as spreading pressure and extrusion molding speed, can be feedback-controlled to fabricate structures (conductive resin sheet and the like) with uniformity higher than conventional ones.

In the first exemplary embodiment, although measurement results without object are used as reference, accurate measurement can be performed at the initial position of the object by a separate means. In such a case, characteristics n and k can be promptly calculated from results of THz transmission measurement. Accordingly, acquisition of time-domain waveform by scan of the first stage 15 and calculation by the fitting method become unnecessary, and hence the initial operation can be shortened.

In the foregoing, acquisition of signals of transmission pulses is described, but acquisition of signals of reflection pulses can also be used. In the latter case, pulses undergoing multiple reflections at interfaces in a layer structure can be observed. Therefore, measurement of these pulses is executed, and operation similar to the above is performed. Further, where both of reflection and transmission pulses are analyzed, more information of the object can be obtained.

A second exemplary embodiment will be described. In the first exemplary embodiment, measurement of Δt and ΔA is performed at each measurement point of the object, and Δd and Δρ are successively calculated to obtain images of distributions of thickness and resistivity. Actually, however, in a case of the sheet-like object as in the first exemplary embodiment, distributions of thickness and resistivity ρ have different patterns as described above referring to FIG. 8A and FIG. 8B.

Accordingly, in the second exemplary embodiment, where two-dimensional pattern or directional property is known from two-dimensional data series of (Δt, ΔA), signal separation is executed by one-dimensional spatial filtering. For example, a filter with 8-mm cutoff is used. When a low pass filter with cutoff below 8 mm is used, calculation is executed on the assumption that the thickness is uniform and the resistivity distribution has a short variation period. Conversely, when a high pass filter with cutoff above 8 mm is used, calculation is executed on the assumption that the resistivity is uniform and the thickness is distributed.

In a case where values of characteristic of the object are beforehand known to have distributions with different periods, precise examination can be rapidly achieved by such signal processing using the spatial filter.

A third exemplary embodiment will be described. In the third exemplary embodiment, an object is placed so that reflection wave pulses can be used. There can be a case where an object has a roll-like configuration, and a roll-like object 100 is examined while being rotated by a roller 101 as illustrated in FIG. 4A. In such a case, where a THz wave detector can be inserted into the roll-like object, the above-described transmission measurement can be used. However, where a space is small, or where reflective matter, such as a metal plate, is disposed in the roll-like object, THz wave reflected in a direction 103 can be analyzed.

In the reflection measurement case, since precision of reflection position largely influences the shift amount of peak time position, a stationary plate 102 is to be placed so that relative positions of the object to THz wave generator and detector do not vary. The stationary plate 102 can be a planar plate of Al (aluminum) capable of acting as a reflector. Reflection THz wave transmitted through the object 100 twice is detected for examination of the object. Such reflection measurement can be performed to an object whose location for transmission measurement is hard to achieve.

A fourth exemplary embodiment will be described. The fourth exemplary embodiment relates to a method of examining food, for example, gum, in which saccharides, such as glucose, is dispersed. A fiber laser is used as exciting light source in the THz-TDS system. The above titanium sapphire laser can also be used. In an ordinary fiber laser, optical fiber doped with rare earth, such as Er, is used as amplifying medium. Fiber lasers capable of oscillating in about 1.55-micron band have been developed. Further, ultrashort pulse laser of 10-femtosecond level is also entirely formed by using optical fibers. Structures using fiber lasers are much smaller in size and much lower in cost than structures using solid lasers. Moreover, the former has high oscillation stability.

Where fiber laser is used as THz wave generating source, photoconductive device using LT-GaAs as described in the above embodiment can be used when illumination of 780-nm band light is performed by using harmonics generator of non-linear crystal or the like. On the other hand, when emission is performed with 1.55-micron or 1.06-micron band THz wave capable of being directly generated from fiber laser, LT-InGaAs epitaxial layers on InP substrate or GaAs substrate can be used.

Figure 4C:
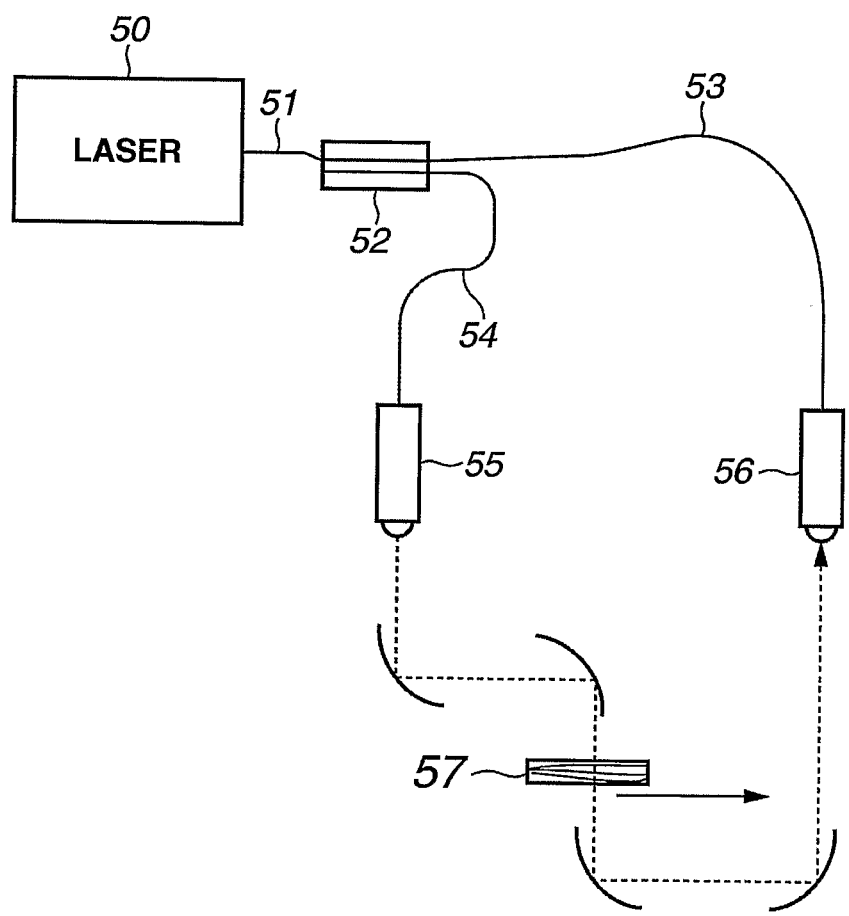

In the fourth exemplary embodiment, as illustrated in FIG. 4C, output from a fiber laser 50 is coupled to THz wave generator 55 and detector 56 by using optical fibers 51, 53 and 54. Accordingly, adjustment of optical axis is facilitated. Fiber coupler 52 divides the output from the fiber laser 50 into two. Each of THz wave generating module 55 acting as THz wave generator and THz wave detecting module 56 acting as detector is an integrated unit including a portion for condensing laser light, light delay portion, photoconductive device, a window for THz wave generation or detection, and lens for controlling direction of wave. In the configuration illustrated in FIG. 4C, a portion of electric system illustrated in FIG. 1 is omitted.

THz wave generator 55 and detector 56 include long-stroke light delay portion and short-stroke light delay portion, respectively. The entire light delay portion can be formed by using optical fibers. In this case, refractive index of fiber medium can be changed by regulating electric field or temperature applied thereto, so that transmission delay occurs. Time delay can be regulated for each frequency by using fiber gratings or the like.

Figure 6E:
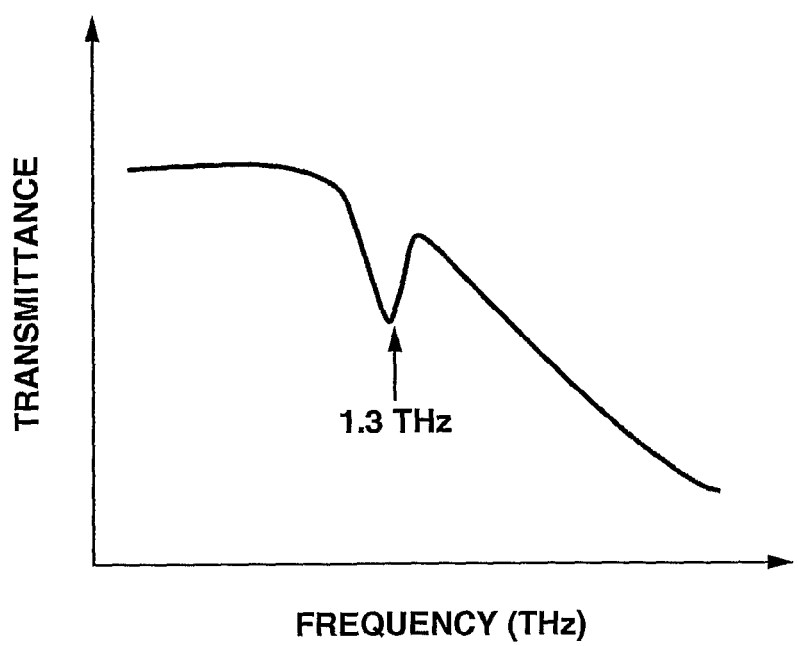

When gum is to be examined, there is a fingerprint spectrum specific to saccharides, such as glucose, contained in the gum. In the fourth exemplary embodiment, characteristic absorption spectrum exists near 1.3 THz as illustrated in FIG. 6E. Data to be beforehand acquired is as follows. One is a value of difference Δa of 1.3-THz absorbance from its standard value appearing as the mixing ratio of saccharides changes in an examination object with a given thickness, and the other is a value of phase difference Δθ of THz wave pulse from its standard value appearing as the mixing ratio of saccharides changes in the object.

Similar to the above embodiment, the object is inserted, and the object is irradiated with THz wave pulse while being moved. Data is acquired at each measurement point. Operation of the system at the initial position is the same as that in the above embodiment. In other words, pulse peak shift in object-inserted state from object-lacking state is acquired, and the pulse peak is tracked. In the fourth exemplary embodiment, information of frequency spectrum is also necessary. Therefore, after the first delay stage is moved to obtain THz waveform, FFT spectrum is calculated so that absorbance shift at 1.3 THz in object-inserted state from object-lacking state is extracted. Thus, based on peak shift amount and absorbance shift amount, thickness and containing amount of saccharides of target composition at the initial position are acquired.

Thereafter, acquisition of peak shift amount from the initial position by the peak tracking, and acquisition of change amount of spectral intensity at 1.3 THz from the initial value by FFT of time-domain waveform obtained by the scan of time delay are performed over all the examination surface. Thereby, based on calculated values at the initial position and change amounts at each measurement point, in addition to relationship data between (ΔA, Δt) of absorbance change at aimed frequency and peak shift time, and (Δd, Δn) of changes of thickness and containing amount, two-dimensional image distributions of thickness and containing amount can be obtained. The relationship data is beforehand measured and stored.

Thus-obtained information can be used for screening based on in-situ examination or feedback control of fabrication parameters, similarly to the above embodiment. Further, calculation speed at initial position can be increased when accurate measurement of thickness is executed at the initial position, similarly to the above embodiment.

Where information at specific frequency is to be used, examination time is somewhat increased since time-domain waveform of THz wave pulse must be acquired. In the fourth exemplary embodiment, however, image of concentration distribution of target composition contained in the object can be obtained in non-contact and non-destructive manner.

A fifth exemplary embodiment will be described. The fifth exemplary embodiment relates to examination of characteristic of cut filter with 10-micron infrared band as aimed radiation. A portion of optical system in the examining apparatus is the same as that illustrated in FIG. 4B. Quantum cascade laser capable of oscillating 10-micron wave is used as the THz wave generator 121. MCT (HgCdTe) semiconductor photodiodes for long wavelength band are used as detectors 122 and 124.

Filter of an object to be examined is placed at position 123. While two-dimensional scan is performed, phase change and transmission intensity change are acquired by using detectors 122 and 124, respectively. Based on the beforehand-acquired relationship data between change amounts of phase and transmission intensity, and changes of thickness and attenuation amount, distributions of thickness and attenuation amount of the infrared filter can be calculated, and imaging thereof can be executed.

In the present invention, there is no limitation to wavelength band of radiation. Micro wave, millimeter wave, THz wave, light wave and the like can be used.

Aspects of the present invention can also be realized by a computer of a system or apparatus (or devices such as a CPU or MPU) that reads out and executes a program recorded on a memory device to perform the functions of the above-described embodiments, and by a method, the steps of which are performed by a computer of a system or apparatus by, for example, reading out and executing a program recorded on a memory device to perform the functions of the above-described embodiments. For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-000465, filed Jan. 5, 2009, which is hereby incorporated by reference herein in its entirety.

The invention claimed is:

1. An apparatus for examining an object whose thickness is unknown, comprising:
    an irradiating portion for irradiating an object with radiation;
    a detecting portion for detecting radiation from the irradiated object;
    an acquiring portion for acquiring transmission time of the radiation from the irradiating portion, which is associated with detection time of the radiation detected by the detecting portion, and amplitude of the radiation detected by the detecting portion;
    a storing portion for beforehand storing relationship data between the transmission time and amplitude, and representative values of characteristic of the object; and
    a calculating portion for obtaining values of thickness and characteristic of the object based on the transmission time, the amplitude and the relationship data stored in the storing portion,
    wherein the representative values of characteristic of the object are values of a complex refractive index or a characteristic of the object capable of being derived from the complex refractive index, and
    wherein the calculating portion simultaneously obtains the values of thickness and characteristic of the object by converging the value of the thickness of the object so that the values of the complex refractive index or the calculated characteristic of the object are fitted to the relationship data.

2. An examining apparatus according to claim 1, wherein the radiation contains a frequency component in a frequency range between 30 GHz and 30 THz.

3. An examining apparatus according to claim 2, wherein the radiation is a pulse, the acquiring portion acquires the transmission time and the amplitude by time domain spectroscopy, and the calculating portion compares the transmission time and the amplitude with the relationship data.

4. An examining apparatus according to claim 3, wherein while a change amount of a peak time position corresponding to the transmission time of the pulse and a change amount of a peak amplitude corresponding to the amplitude of the pulse are stored as a relative position of the object relative to the pulse is moved, the values of thickness and characteristic of the object are obtained at each relative position by the calculating portion, and imaging of distributions of the thickness and the characteristic of the object is performed.

5. A method of driving an examining apparatus according to claim 4, the method comprising:
    a step of moving the relative position of the object relative to the pulse;
    a step of feedback-controlling a delay position of a delay portion used in time domain spectroscopy so that the peak time position of the pulse is always maintained to be acquired in the moving step; and
    a step of storing the delay position feedback-controlled in the controlling step.

6. An examining apparatus according to claim 1, wherein the characteristic of the object obtained by the calculating portion is electric conductivity or resistivity.

7. An examining apparatus according to claim 1, wherein the object has absorption at a specific frequency, the storing portion beforehand stores amplitude at the specific frequency as the amplitude of the radiation, and the calculating portion obtains the values of the thickness and the characteristic of the object based on the amplitude at the specific frequency and the relationship data.

8. An examining apparatus for examining an object comprising:
    an irradiating portion for irradiating an object with radiation;
    a detecting portion for detecting radiation from the irradiated object;
    an acquiring portion for acquiring transmission time of the radiation from the irradiating portion, which is associated with detection time of the radiation detected by the detecting portion, and amplitude of the radiation detected by the detecting portion;
    a storing portion for beforehand storing relationship data between the transmission time and amplitude, and representative values of characteristic of the object; and
    a calculating portion for obtaining values of thickness and characteristic of the object based on the transmission time, the amplitude and the relationship data stored in the storing portion,
    wherein the radiation contains a frequency component in a frequency range between 30 GHz and 30 THz, wherein the radiation is a pulse, the acquiring portion acquires the transmission time and the amplitude by time domain spectroscopy, and the calculating portion compares the transmission time and the amplitude with the relationship data, wherein while a change amount of a peak time position corresponding to the transmission time of the pulse and a change amount of a peak amplitude corresponding to the amplitude of the pulse are stored as a relative position of the object relative to the pulse is moved, values of thickness and characteristic of the object are obtained at each relative position by the calculating portion, and imaging of distributions of the thickness and the characteristic of the object is performed, and wherein the distributions of the thickness and the characteristic of the object are separated by using a spatial filter after the imaging is performed.

9. An examining method of examining an object whose thickness is unknown, the method comprising:

a detecting step of detecting radiation from an object irradiated with the radiation;

an acquiring step of acquiring transmission time associated with detection time of the radiation detected in the detecting step, and amplitude of the radiation detected in the detecting step;

a storing step of beforehand storing relationship data between the transmission time and amplitude, and representative values of characteristic of the object; and a calculating step of obtaining values of thickness and characteristic of the object based on the transmission time and amplitude acquired in the acquiring step and the relationship data stored in the storing step, wherein the representative values of characteristic of the object are values of a complex refractive index or a characteristic of the object capable of being derived from the complex refractive index, and wherein the calculating step simultaneously obtains the values of thickness and characteristic of the object by converging the value of the thickness of the object so that the values of the complex refractive index or the calculated characteristic of the object are fitted to the relationship data.

* * * * *